US00PP07811P

United States Patent [19]

Meilland

[11] Patent Number: Plant 7,811

[45] Date of Patent: Mar. 3, 1992

[54] ROSE PLANT—MEIBLONVER VARIETY

[75] Inventor: Alain A. Meilland, Antibes, France

[73] Assignee: The Conard-Pyle Company, West Grove, Pa.

[21] Appl. No.: 580,254

[22] Filed: Sep. 10, 1990

[51] Int. Cl.[5] ..... A01H 5/00
[52] U.S. Cl. ..... Plt./15
[58] Field of Search ..... Plt. 11, 14, 15, 22, Plt./23, 24

*Primary Examiner*—Howard J. Locker

*Attorney, Agent, or Firm*—Burns, Doane, Swecker & Mathis

[57] ABSTRACT

A new and distinct variety of hybrid tea rose plant is provided which forms attractive double long lasting blossoms which are of an attractive pale cream white coloration. The plant forms buds having a very elegant shape, exhibits an upright growth habit, forms vigorous vegetation, and is well suited for greenhouse forcing during cut flower production. Additionally, the plant is not particularly affected by cryptogamic diseases.

1 Drawing Sheet

SUMMARY OF THE INVENTION

The new variety of hybrid tea rose plant was created by artificial pollination wherein two parents were crossed which previously had been studied in the hope that they would contribute the desired characteristics. The female parent (i.e., the seed parent) of the new variety was the Emily Post variety (U.S. Plant Pat. No. 3,749). The male parent (i.e., the pollen parent) was the Jelpirofor variety (U.S. Plant Pat. No. 5,632). The parentage of the new variety can be summarized as follows:

Emily Post×Jelpirofor.

The seeds resulting from the above pollination were sown and 5 small plants were obtained which were physically and biologically different from each other. Selective study resulted in the identification of a single plant of the new variety.

It was found that the new variety of hybrid tea rose plant of the present invention possesses the following combination of characteristics:

(a) forms attractive long lasting double blossoms which are of an attractive pale cream white coloration,
(b) exhibits an upright growth habit,
(c) exhibits vigorous vegetation,
(d) is particularly suited for greenhouse forcing in the production of cut flowers, and
(e) is not particularly affected by cryptogamic diseases.

The new variety forms buds having a very elegant configuration.

The new variety well meets the needs of the horticultural industry and is particularly suited for use in the production of fresh cut flowers.

The new variety has been found to undergo asexual propagation by a number of routes, including budding, grafting, and cuttage. Asexual propagation by the above mentioned methods as performed in France shows that the characteristics of the new variety are strictly transmissible from one generation to another and appear to be firmly fixed.

The new variety has been named the Meiblonver variety.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety were three years of age and were observed during February while budded on *Rosa indica* understock and growing in greenhouses at Cap d'Antibes, France.

FIG. 1—illustrates a specimen of a young shoot;

FIG. 2—illustrates a specimen of a floral bud before the opening of the sepals;

FIG. 3—illustrates a specimen of a floral bud at the opening of the sepals;

FIG. 4—illustrates a specimen of a floral bud at the opening of the petals;

FIG. 5—illustrates a specimen of a flower in the course of opening;

FIG. 6—illustrates a specimen of an open flower—plan view—obverse;

FIG. 7—illustrates a specimen of an open flower—plan view—reverse;

FIG. 8—illustrates a specimen of a fully open flower—plan view—obverse;

FIG. 9—illustrates a specimen of a fully open flower—plan view—reverse;

FIG. 10—illustrates a specimen of a floral receptacle showing the arrangement of the stamens and pistils.

FIG. 11—illustrates a specimen of a floral receptacle showing the arrangement of the pistils (stamens removed);

FIG. 12—illustrates a specimen of a flowering stem;

FIG. 13—illustrates a specimen of a main branch;

FIG. 14—illustrates a specimen of a leaf with three leaflets—plan view—lower surface;

FIG. 15—illustrates a specimen of a leaf with five leaflets—plan view—upper surface; and FIG. 16—illustrates a specimen of a leaf with seven leaflets—plan view—under surface.

DETAILED DESCRIPTION

Figures 1, 2, 3, 4, 5, 6, 7, 8, 9, 10, 11, 12, 13, 14, 15, 16:
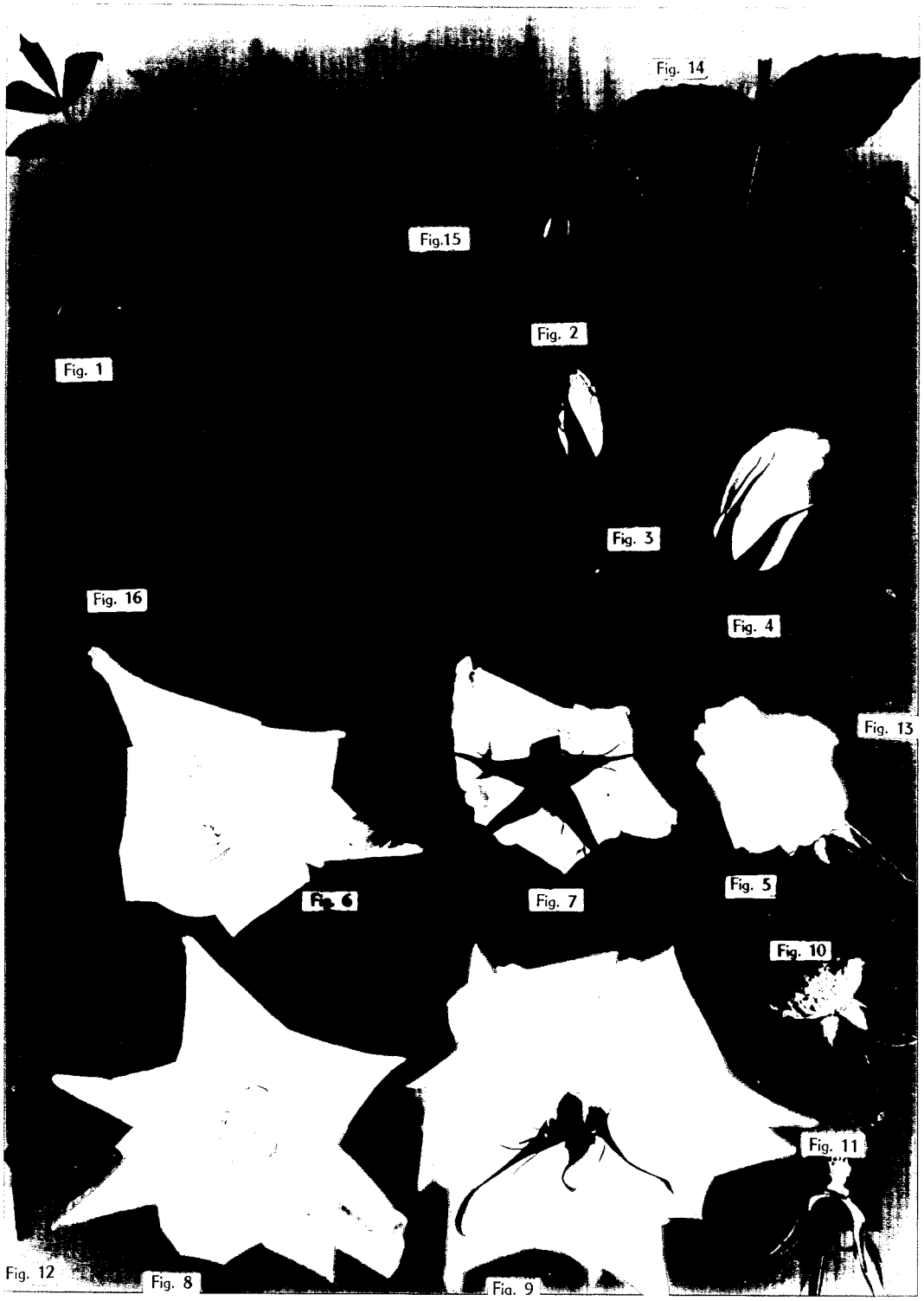

The chart used in the identification of the colors is that of the Royal Horticultural Society (R.H.S. Colour Chart). The description is based on the observation of three year old plants made during February while budded on *Rosa indica* understock and growing in greenhouses at Cap d'Antibes, France. The coloration in common terms precedes reference to the chart.

Class: Hybrid tea.

Plant:

*Height.*—When plants are cut to a height of approximately 85 cm., flowering stems having a length of approximately 40 to 60 cm. commonly are produced. When grown outdoors at Wasco, Calif., U.S.A., at the end of the growing season the average plant height is approximately 100 to 110 cm.

*Habit.*—Upright.

Branches:

*Color.*—Young stems: light green, Green Group 143C, more or less stained with reddish coloration. Adult wood: medium green, Green Group 143B.

*Thorns.*—Size: small to medium. Quantity: very few, and sometimes totally absent on young stems during the winter. Color: pinkish on young stems and greenish-pink changing to tan on mature wood.

Leaves:

*Stipules.*—Adnate, pectinate, wide and linear.

*Petioles.*—Upper surface: striped reddish brown on young foliage and medium green on mature foliage with more or less glandular edges. Under surface: light green, bear a few prickles.

*Leaflets.*—Number: 3, 5 and 7. Shape: spear-like. Serration: single and regular. Texture: consistent. General appearance: fairly dense, bright foliage. Color (young foliage): upper surface: medium green, Green Group 143A, more or less stained with reddish brown coloration. under surface: light green, Green Group 143B, edged and more or less stained with reddish coloration. Color (adult foliage): upper surface: dark green, Green Group 137A. under surface: medium green, Green Group 138B.

Inflorescence:

*Number of flowers.*—Usually one single bloom per stem, but sometimes 1 to 5 blooms per stem.

*Peduncle.*—Light green, bears a few pediculate glands. The length is approximately 8 to 10 cm. on average.

*Sepals.*—Upper surface: greenish tomentose. under surface: light green, the outer sepals have edges that are only slightly appendiculated.

*Buds.*—Shape: oblong. Length: approximately 3 cm. on average. Size: medium. Color (upon opening): upper surface: pale cream white, Yellow Group 4D, more or less suffused with light chartreuse, Yellow-Green Group 154D. under surface: pale cream white, Yellow Group 4D, more or less suffused with light chartreuse, Yellow-Green Group 154D.

*Flower.*—Shape: shallow cup. Diameter: approximately 11 cm. on average. Color (when opening begins): upper surface: pale cream white, Yellow Group 4D, more or less suffused with light chartreuse, Yellow-Green Group 154D. under surface: pale cream white, Yellow Group 4D, more or less suffused with light chartreuse, Yellow-Green Group 154D. Color (when blooming): upper surface: pale cream white, Yellow Group 4D. under surface: pale cream white, Yellow Group 4D. Color (at end of opening): upper surface: pale cream white, Yellow Group 4D. under surface: pale cream white, Yellow Group 4D.Fragrance: none. Lasting quality: long, and normal for a fresh cut flower variety, commonly last approximately 7 to 9 days when placed in a vase. Petal number: approximately 25 on average. Texture: fairly consistent. Petal drop: good. Stamen number: approximately 169 on average. Anthers: ochre, normal. Filaments: free standing, straw in coloration, of irregular heights. Pistils: approximately 147 on average. Stigmas: normal, straw colored. Styles: free-standing, greenish straw in coloration, of irregular heights. Receptacle: in longitudinal section it is wide and in the shape of a pitcher.

Development:

*Vegetation.*—Fairly vigorous.

*Blooming.*—Fairly abundant.

*Resistance to diseases.*—Good.

*Aptitude to be forced.*—Good.

I claim:

1. A new and distinct variety of Hybrid Tea rose plant characterized by the following combination of characteristics:

(a) forms attractive long lasting double blossoms which are of an attractive pale cream white coloration,
(b) exhibits an upright growth habit,
(c) exhibits vigorous vegetation,
(d) is particularly suited for greenhouse forcing in the production of cut flowers, and
(e) is not particularly affected by cryptogamic diseases;

substantially as herein shown and described.

* * * * *